United States Patent [19]
Yasushi et al.

[11] Patent Number: 6,104,296
[45] Date of Patent: Aug. 15, 2000

[54] BIOLOGICAL INFORMATION DETECTION APPARATUS

[75] Inventors: Mitsuo Yasushi; Masatoshi Yanagidaira; Jun Cheng; Kayoko Takashima, all of Tokyo-to, Japan

[73] Assignee: Pioneer Electronic Corporation, Tokyo, Japan

[21] Appl. No.: 09/251,428

[22] Filed: Feb. 17, 1999

[30]      Foreign Application Priority Data

Feb. 18, 1998  [JP]  Japan ................................... 10-052813

[51] Int. Cl.⁷ .................................................. G08B 23/00
[52] U.S. Cl. ...................... 340/576; 340/465; 340/573.1; 180/272; 701/1; 600/301
[58] Field of Search ..................................... 340/576, 465, 340/575, 573.1, 425.5; 180/271, 272; 701/1; 600/301

[56]                  References Cited

U.S. PATENT DOCUMENTS

| | | | |
|---|---|---|---|
| 4,438,425 | 3/1984 | Tsuchida et al. ......................... | 340/465 |
| 4,456,903 | 6/1984 | Kishi et al. .............................. | 340/465 |
| 4,706,072 | 11/1987 | Ikeyama ................................... | 340/576 |
| 5,453,929 | 9/1995 | Stove ........................................ | 340/575 |
| 5,574,641 | 11/1996 | Kawakami et al. ..................... | 340/576 |
| 5,585,785 | 12/1996 | Gwin et al. .............................. | 340/576 |

*Primary Examiner*—Nina Tong
*Attorney, Agent, or Firm*—Morgan, Lewis & Bockius LLP

[57]                  ABSTRACT

A biological information detection apparatus including a biological information detection and transmission unit mounted on a steering wheel for detecting and transmitting biological information of an operator of a motor vehicle; a biological information receiver mounted on a steering column that receives biological information detection and transmission unit; and a steering wheel position detector that detects a rotational position of the steering wheel; wherein the biological information detection and transmission unit includes a sensor for detecting biological information and generating a detection signal memory for storing the detection signal from the sensor; a transmitter for transmitting a detection signal from the memory; and a controller for controlling the storage of the detection signal in memory and the transmitting of the detection signal from the transmitter when the steering wheel position detector detects that the steering wheel is in a substantially straight driving position; and the biological information receiver includes a receiver which is mounted in a position whereby a detection signal from the transmitter can be received wirelessly when the steering wheel is in a substantially straight driving position.

18 Claims, 5 Drawing Sheets

BIOLOGICAL INFORMATION DETECTION APPARATUS

This invention claims the benefit of Japanese Patent Application No. 10-052813, filed on Feb. 18, 1998.

BACKGROUND OF THE INVENTION

1. Field of the Invention

The present invention relates to a biological information detection apparatus for detecting a driver's biological status information, such as heart beat rate and brain wave signals, while the person is driving or operating an automobile, boat, aircraft, or other vehicle.

2. Discussion of the Related Art

Devices have been proposed in recent years for monitoring the health of an operator of a motor vehicle by monitoring the operator's heart beat rate while driving to detect operator drowsiness, fatigue, irritability, or arrhythmia. Such devices typically have a sensor, such as a heart beat sensor, fastened to a steering wheel. The devices evaluate operator health based on the heart rate obtained from the heart beat sensor. A signal detected by such a sensor is typically transmitted by a wire harness inside the steering wheel, hub, and steering column to an evaluation device or other signal processing unit. These conventional monitoring devices are expensive because the steering wheel and column are generally standard safety components that must be redesigned in order to additionally incorporate the monitoring apparatus.

To alleviate the costs of retrofitting, it is conceivable to use a standard steering wheel and column by transmitting detection signals from the sensor through a wire harness disposed externally to the steering wheel and column. However, in this configuration, the harness may be subject to short circuits as the steering wheel is turned during driving, and the wires may become wound around the steering wheel. This can lead to potentially dangerous situations while driving.

SUMMARY OF THE INVENTION

Accordingly, the present invention is directed to a biological information detection apparatus that substantially obviates one or more of the above problems due to the limitations and disadvantages of the related art.

An object of the invention is to provide a biological information detection apparatus that does not require retrofitting the steering wheel or column and eliminates wire harness short circuits and winding of wire around the steering column.

Another object of the invention is to provide a biological information detection apparatus in which a receiving means is preferably mounted in a position opposite a transmission means when the steering wheel is in a substantially straight driving position.

Yet another object of the present invention is to provide a biological information detection apparatus that comprises a diagnostic unit that diagnoses a health-related condition of an operator based on the detection signal received by the receiver, and a notification unit that notifies the operator of the diagnostic result obtained by the diagnostic unit.

According to one aspect of the present invention, the transmitter contains a light-emitting element for transmitting the detection signal as an optical signal, and the receiver contains a receptor element for receiving said optical signal.

According to another aspect of the present invention, the steering wheel position detector preferably comprises at least one light-emitting element and receptor element pair disposed in opposition on the steering wheel and steering column part when the steering wheel is in a substantially straight driving position.

According to a further aspect of the present invention, the detection signal received by the receiver is wirelessly transmitted, and the diagnostic unit receives the wirelessly transmitted detection signal.

To achieve these and other advantages and in accordance with the purpose of the present invention, as embodied and broadly described, a biological information detection apparatus according to the present invention includes a biological information detection and transmission unit that is mounted on a steering wheel for detecting and transmitting biological information of an operator of a motor vehicle; a biological information receiver which is mounted on a steering column that receives biological information from the biological information detection and transmission unit; and a steering wheel position detector that detects a rotational position of the steering wheel. In this biological information detection apparatus the biological information detection and transmission unit includes a sensor for detecting biological information, memory for storing a detection signal from the sensor, a transmitter means for transmitting a detection signal from the memory, and a controller for controlling reading a detection signal stored in memory and the transmitting of the said detection signal from the transmitter when the steering wheel position detector detects that the steering wheel is in a substantially straight driving position.

Furthermore, the biological information receiver includes a receiver which is mounted in a position whereby a detection signal from the transmitter can be received wirelessly when the steering wheel is in a substantially straight driving position.

BRIEF DESCRIPTION OF THE DRAWINGS

The accompanying drawings, which are included to provide a further understanding of the invention and are incorporated in and constitute a part of the specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
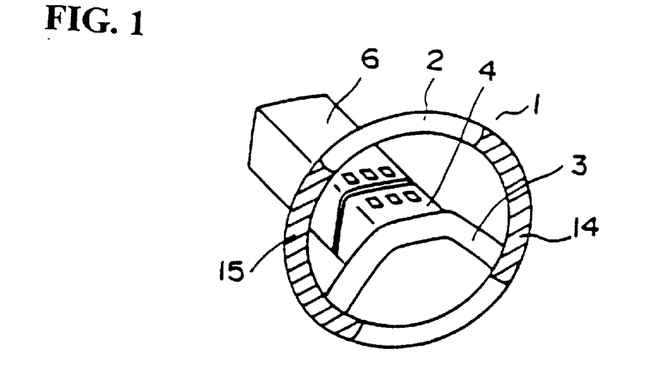
FIG. 1 illustrates a steering wheel assembly and steering column assembly of an apparatus according to the present invention.
Figure 2:
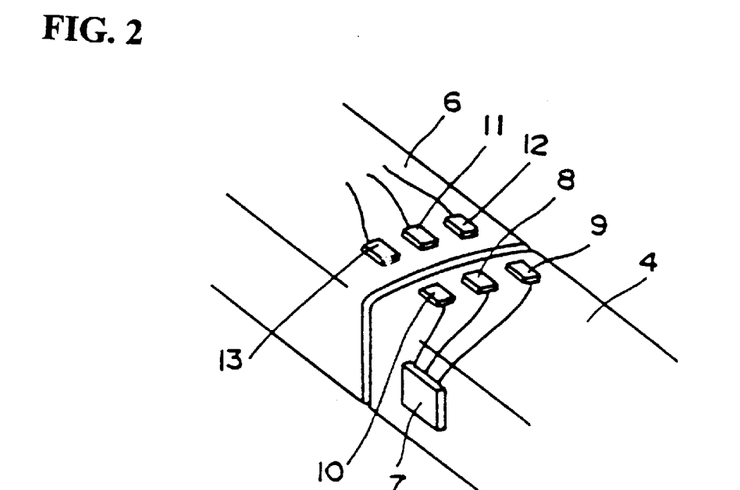
FIG. 2 illustrates the infrared emitter and receptive devices along the steering wheel assembly and steering column assembly according to the present invention.
Figure 3:
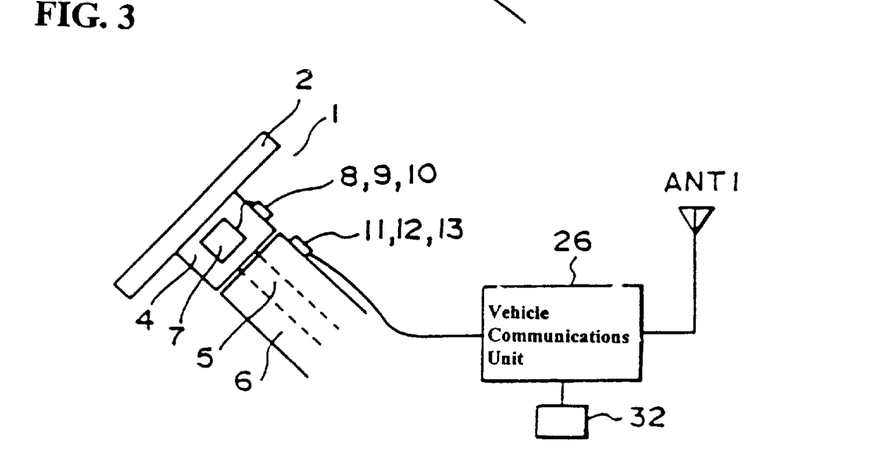
FIG. 3 is a side view of the steering wheel assembly and steering column assembly connected with a vehicle communications unit according to the present invention.

FIGS. 1 to 3 show a steering wheel assembly and steering column assembly according to the present invention. The steering wheel assembly 1 comprises a steering wheel 2, a spoke 3 for supporting the steering wheel 2, a hub 4 for supporting the spoke 3, and a steering shaft 5. The steering column part 6 axially supports the steering shaft 5 of the steering wheel assembly in a freely rotating manner.

An infrared receptor 8 is mounted to the top center area of the hub 4 of the steering wheel part 1. Infrared emitters 9 and 10 are disposed on both sides of the infrared receptor 8. A pair of electrodes 14 and 15 are disposed on the surface on the right and left sides of the steering wheel 2. These electrodes detect the driver's heart beat as the biological information of interest. A heart beat data transmission device 7 is disposed on a side of the hub 4, as a biological information detection and transmission unit.

An infrared emitter 11 is located at the top middle of the steering column part 6, between two infrared receptors 12 and 13. The infrared receptor 8 and infrared emitter 11, and the infrared emitters 9 and 10 and infrared receptors 12 and 13, are positioned such that they are mutually aligned when the steering wheel part 1 is positioned for driving in a substantially straight line. When the vehicle is steered in a straight line by means of the steering wheel 2, the infrared receptor 8 and infrared emitter 11, and the infrared emitters 9 and 10 and infrared receptors 12 and 13, are respectively positioned in opposition with no contact therebetween. The infrared receptor 8 and infrared emitter 11 detect the turning position of the steering wheel part 1. The infrared emitter 11 and infrared receptors 12 and 13 are connected to a vehicle communications unit 26.

Figure 4:
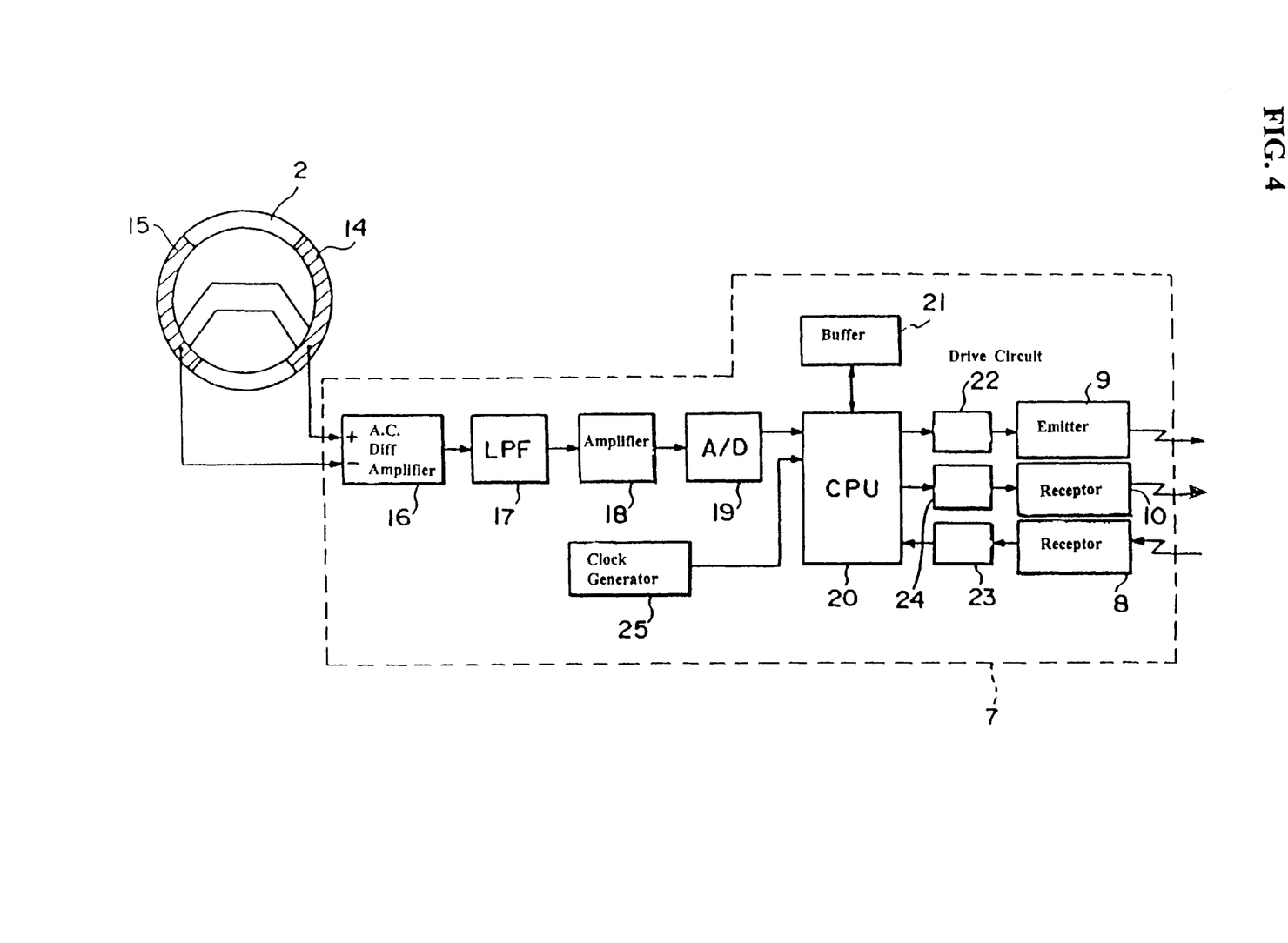
FIG. 4 illustrates a schematic diagram of a heart beat data transmission device according to the present invention.

FIG. 4 illustrates the heart beat data transmission device 7 according to a preferred embodiment of the invention. Reference numerals 8, 9, and 10 denote the above-noted infrared receptor and infrared emitters. AC differential amplifier 16 detects a potential difference between electrodes 14 and 15. Low-pass filter 17 removes extraneous noise components from an output signal of the AC differential amplifier 16. Amplifier 18 amplifies low-pass filter 17 output. Analog-digital converter 19 converts a heart beat signal from the amplifier 18 to a digital signal. CPU 20 controls the operation of the heart beat data transmission device 7 based on the digital heart beat signal input from the A/D converter 19. Buffer 21 temporarily stores the digital heart beat signal. Drive circuit 22 is for driving infrared emitter 9 based on a digital heart beat signal read from the buffer 21 and input by the CPU 20, drive circuit 23 is for amplifying to a specific signal level of a signal from infrared emitter 11 that is received and photoelectrically converted by infrared receptor 8, end drive circuit 24 is for driving infrared emitter 10 based on a clock input thereto by the CPU 20. Clock generator 25 applies an operating clock to the CPU 20.

Figure 5:
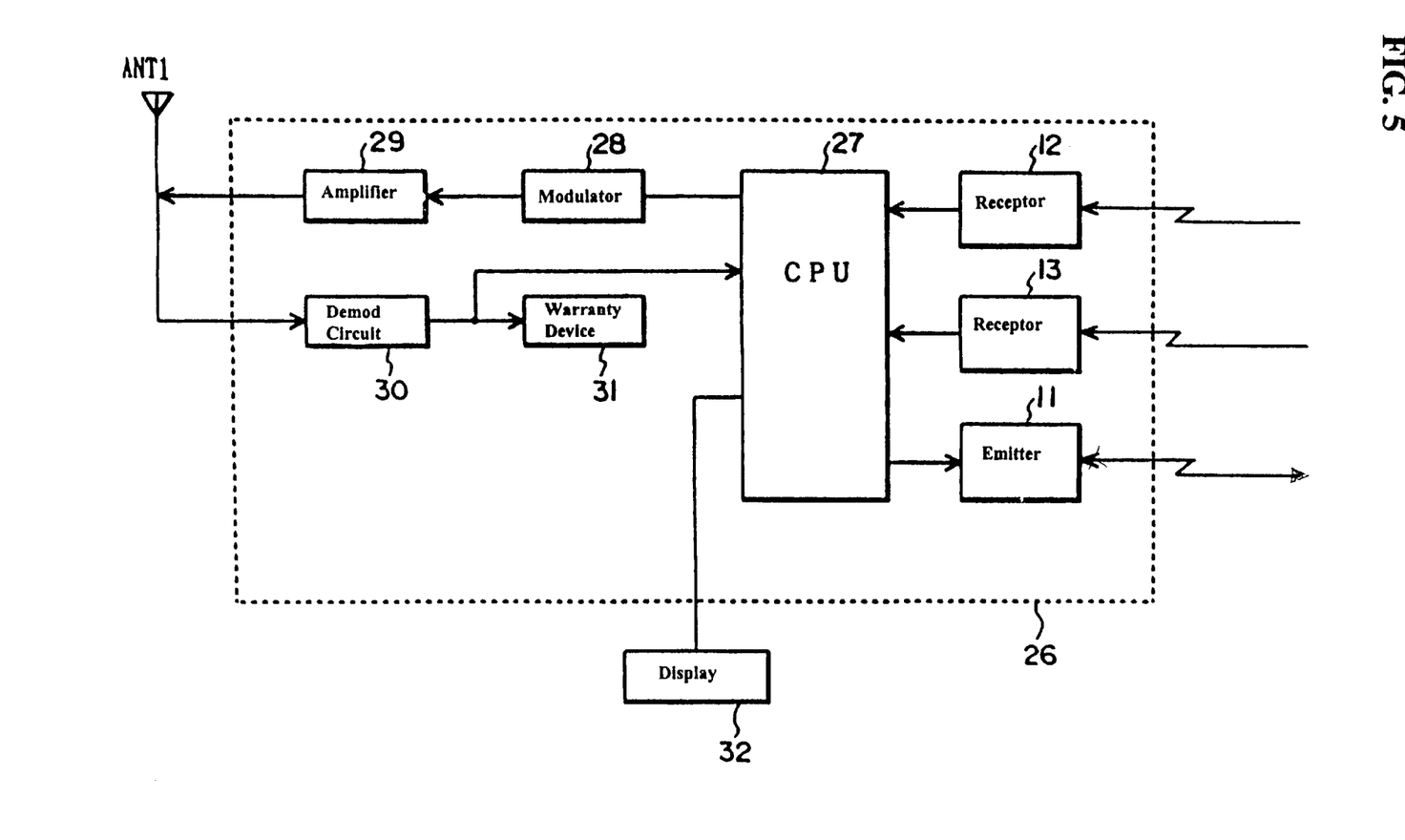
FIG. 5 is a schematic of a diagram of a vehicle communications unit according to the present invention.

FIG. 5 shows the vehicle communications unit 26. In this system, a heart beat signal is wirelessly transmitted from the heart beat data transmission device 7 to an external monitoring device 33 (FIG. 6), and a health condition of the vehicle operator is determined based on the heart beat signal. Vehicle communications unit 26 also contains a biological information receiver for the health condition result transmitted from the monitoring device 33. This vehicle communications unit 26 is mounted in the vehicle.

Referring to FIG. 5, reference numerals 11, 12, and 13 denote the above-noted infrared emitter and infrared receptors; CPU 27 drives the infrared emitter 11 to cause an infrared beam to be generated, and controls the vehicle communications unit 26 based on signals from the infrared emitters 9 and 10 that are received and photoelectrically converted by the infrared receptors 12 and 13. Element 28 is a modulation circuit for modulating the digital heart beat signal output by the CPU 27. Amplifier 29 is for power amplifying the modulated signal from the modulation circuit 28. Demodulation circuit 30 is for demodulating a warning signal and heart beat data transmitted from the monitoring device 33. Warning device 31 is driven by means of a signal from the demodulation circuit 30. In addition, element 32 shows a display monitor for graphically displaying a warning signal and heart beat data transmitted from the monitoring device 33, and ANT1 is an antenna for sending and receiving radio frequency signals with the monitoring device 33.

Figure 6:
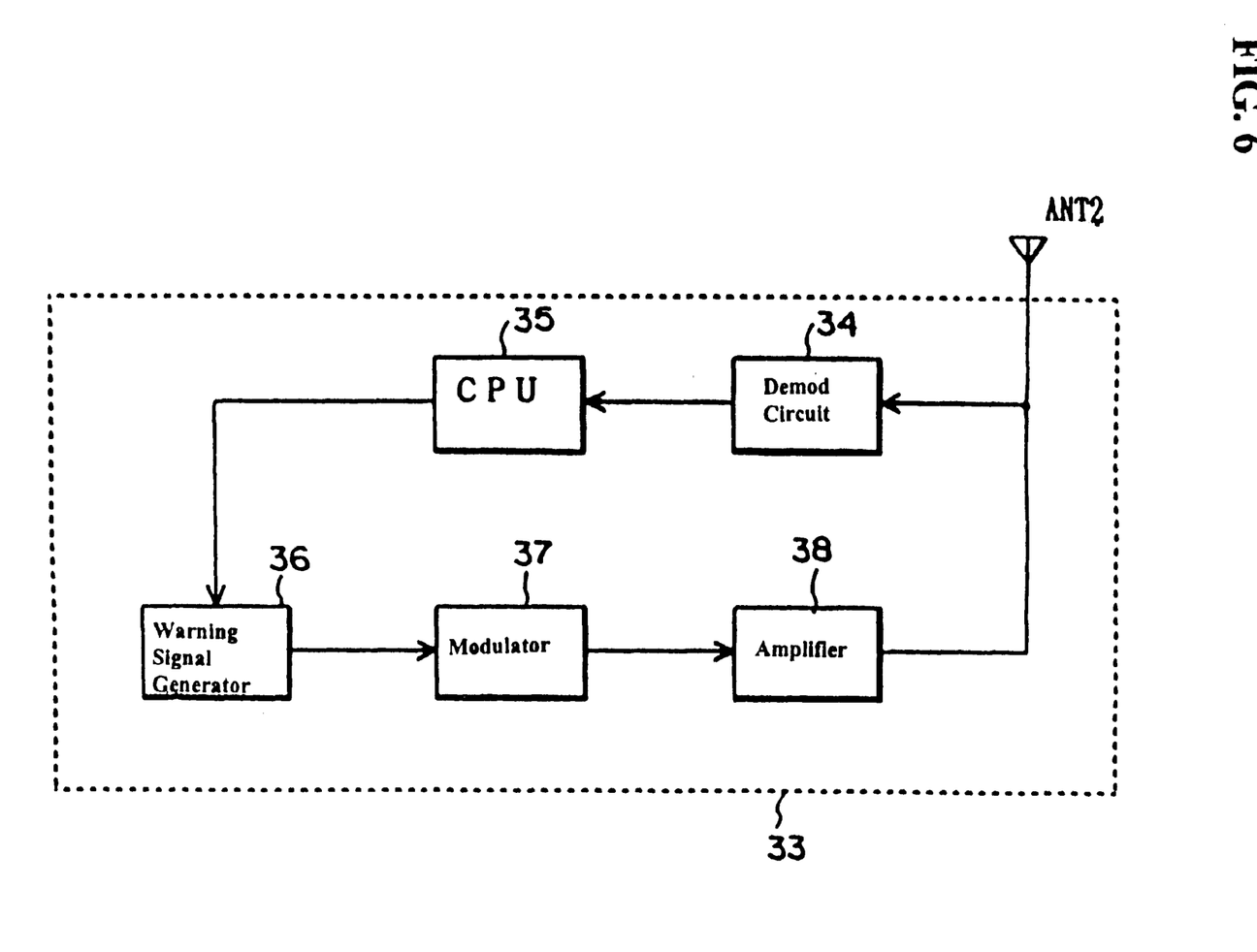
FIG. 6 provides a schematic of a diagnostic device based on biological information in an apparatus according to the present invention.

FIG. 6 shows a monitoring device 33 containing a diagnostic system. In FIG. 6, reference numeral 34 denotes a demodulation circuit for demodulating a modulated signal sent from the vehicle communications unit 26. CPU 35 performs heart beat analysis based on a digital heart beat signal demodulated by the demodulation circuit 34, and diagnoses a health condition of the vehicle operator. Warning signal generator 36 is driven based on the analysis result from the CPU 35. Modulation circuit 37 is for modulating the warning signal from the warning signal generator 36. Amplifier 38 power amplifies the modulated signal from the modulation circuit 37. ANT2 is an antenna for sending and receiving radio frequency signals with the vehicle communications unit 26.

The operation of the biological detecting apparatus now will be described. When an operator holds the steering wheel 2 with both hands in order to drive the vehicle, the operator's hands contact the pair of electrodes 14 and 15 mounted on the surface of the steering wheel 2. The electrodes 14 and 15 form a potential-type heart beat sensor such as is known in the art, and detect the pulse potential (cardiac action potential) between the driver's hands accompanying electric stimulation of the heart from the electrodes 14 and 15 to detect the heart beat. The voltage detected by the electrodes 14 and 15 is input to AC differential amplifier 16 to detect the potential difference between electrodes 14 and 15. The output from the AC differential amplifier 16 is input to the low-pass filter 17, which removes extraneous noise, such as noise produced by the vehicle, and passes only a 20-Hz heart beat signal component (approximately 20 Hz). The heart beat signal passed by the low-pass filter 17 is amplified to a specific level by the amplifier 18, and is then converted to a digital signal by the A/D converter 19. The digital heart beat signal waveform, that is, the digital cardiac action potential data, is input to the CPU 20, and is temporarily stored in the buffer 21 by the CPU 20. The input time of the digital heart beat data to the CPU 20, which is indicative of the time that the driver's heart beat was detected, is also stored concurrently with the cardiac action potential data. It should be noted that the clock generator 25 supplies an operating clock to the CPU 20.

A drive signal is applied to the infrared emitter 11 of the vehicle communications unit 26 by CPU 27, and the infrared emitter 11 is in a constantly emitting state while the vehicle is moving. When the driver is holding the steering wheel 2 of the steering wheel part 1 to drive the vehicle, the infrared receptor 8, disposed at the top middle part of the hub 4, and the infrared emitter 11, disposed at the top middle of the steering column part 6, become offset to a non-opposing position when the vehicle is not traveling in a straight line, such as when traveling through a curve. Since the steering wheel is tilted, the infrared receptor 8 is unable to receive and detect light from the infrared emitter 11. When the steering wheel 2 is thus positioned, the heart beat data and time information stored to the buffer 21 are not read out and remain buffered, and new heart beat data output from the A/D converter 19 is stored with the corresponding time information in the buffer 21.

On the other hand, when the vehicle is traveling straight, the infrared receptor 8, disposed on the hub 4, and the infrared emitter 11, disposed on the steering column part 6 are in opposing positions, and the infrared receptor 8 is thus positioned to receive light from the infrared emitter 11. The infrared receptor 8 photoelectrically converts the detected light and generates a position detection signal as the detection signal is output therefrom to the drive circuit 23. When the detection signal amplified by the drive circuit 23 is applied to the CPU 20, the CPU 20 determines that the steering wheel part 1 is in the driving straight position and reads and outputs the digital heart beat signal and time information stored in the buffer 21 to drive circuit 22. A synchronization clock is simultaneously output to drive circuit 24. Infrared emitters 9 and 10 are driven by output from drive circuits 22 and 24 such that an infrared beam containing the digital heart beat signal and time information is emitted from infrared emitter 9, and an infrared beam containing the clock is emitted from infrared emitter 10.

In this driving straight position, infrared emitter 9 and infrared receptor 12, and infrared emitter 10 and infrared receptor 13, respectfully, are mutually opposed, and receptors 12 and 13 are able to receive infrared beams from the emitters 9 and 10. As a result, the digital heart beat signal and time information received and photoelectrically converted by infrared receptor 12, and the clock received and photoelectrically converted by infrared receptor 13, are input to CPU 27. CPU 27 is thus synchronized based on this clock, sequentially reads the digital heart beat signal and time information, and sequentially outputs to the modulation circuit 28 at a specific timing. The digital heart beat signal and time information are thus modulated with a specific carrier signal, power amplified by the amplifier 29, and transmitted from antenna ANT1.

When the monitoring device 33 receives by means of antenna ANT2 the modulated signal carrying the digital heart beat signal and time information transmitted from the vehicle communications unit 26, the demodulation circuit 34 demodulates the received signal, and passes the demodulated signal to the CPU 35. Using a known method, the CPU 35 calculates the heart rate and other heart beat data from a heart beat signal waveform (electrocardiographic signal), which changes over time and is obtained by the heart beat data transmission device 7. The CPU then performs a heart beat analysis and monitors irregularities, e.g., arrhythmia. If an abnormality is confirmed as a result of this analysis, the CPU 35 outputs a warning drive signal to the warning signal generator 36, which generates a warning signal. This warning signal is modulated by the modulation circuit 37, power amplified by the amplifier 38, and then transmitted from the antenna ANT2.

The warning signal transmitted from antenna ANT2 is received by antenna ANT1 of the vehicle communications unit 26 and demodulated by the demodulation circuit 30. To issue a warning by means of an audio signal or image, the demodulated warning signal is input to the warning device 31, which can be a speaker or display device installed in the vehicle. By recognizing this warning signal, the driver is informed that a health-related problem such as arrhythmia has been detected.

Figure 7:
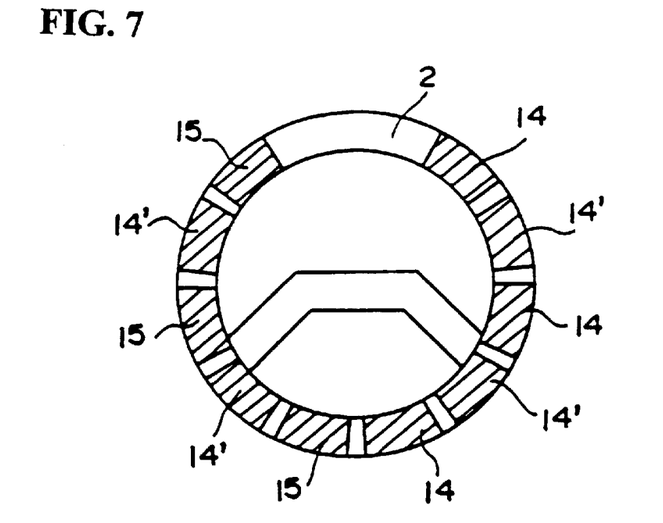
FIG. 7 illustrates an alternative embodiment of a steering wheel assembly in an apparatus according to the present invention.
Figure 8:
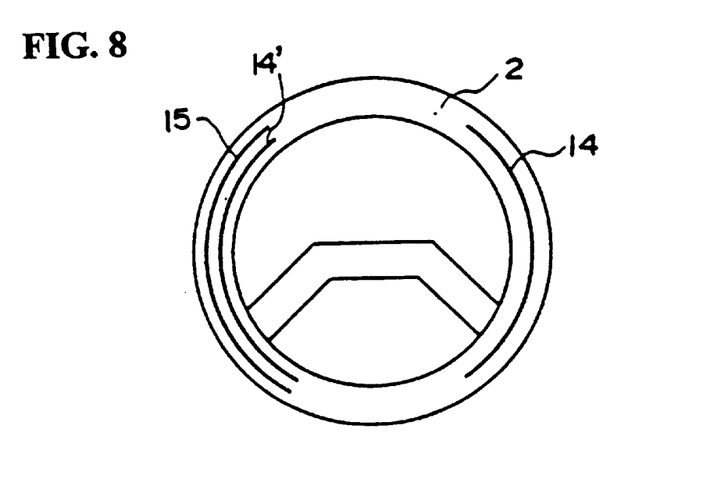
FIG. 8 illustrates an additional embodiment of a steering wheel assembly in an apparatus according to the present invention.

FIG. 7 and FIG. 8 show alternative versions of the heart beat detection electrodes mounted on the steering wheel 2 of the steering wheel part 1.

In the embodiment shown in FIG. 7, a plurality of electrodes 15 and 14' are alternately disposed on one right or left side of the steering wheel 2, and a plurality of electrodes 14 and 14' are alternately disposed on the other side. Electrodes 15 and 14', and electrodes 14 and 14' are electrically isolated.

In the embodiment shown in FIG. 8, metal wire electrodes 15 and 14' are disposed parallel to each other following the line of the steering wheel 2 on one right or left side of the steering wheel 2, and a similar metal wire electrode 14 is disposed on the other side similarly following the line of the steering wheel 2.

Figure 9:
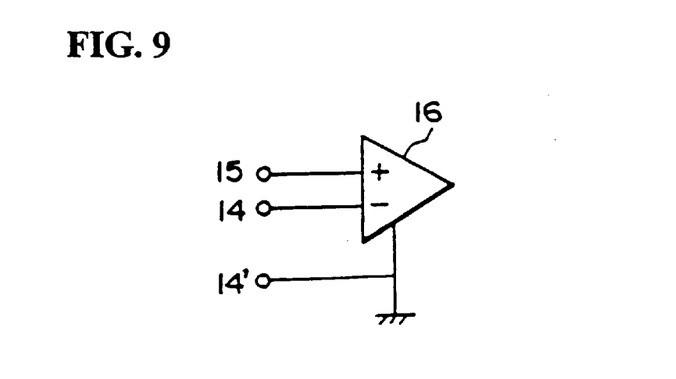
FIG. 9 illustrates a preferred embodiment of a differential amplifier in an apparatus according to the present invention.

The configuration of the differential amplifier 16 in a heart beat data transmission device suitable for use with heart beat detection electrodes is shown in FIG. 9. More specifically, electrode 15 and electrode 14 are connected to the non-inverted input and inverted input of differential amplifier 16, and electrode 14' is grounded. As a result, differential amplifier 16 outputs a potential difference between electrodes 14 and 15 relative to the reference potential of electrode 14'.

When an apparatus according to the invention is used in an operating system for a bus or taxi, the driver's biological information can be transmitted to the monitoring device 33 in real time. The driver's health condition can be analyzed by the monitoring device 33 while driving, and the driver can be immediately notified when a problem is detected. Since arrhythmia can result when operating a motor vehicle, due to stress or from fatigue, particularly in the elderly, major accidents can be prevented by informing the driver that a health-related problem has been detected.

It should be farther noted that when the present invention is deployed in an operating system for a bus or taxi, the biological information detection apparatus can be configured so that the vehicle communications unit 26 only transmits biological information, and the driver is later notified directly when the driver's work duty is over and he or she returns to the monitoring center, garage, or other place where the monitoring device 33 is located.

The present invention also can be adapted to a vehicle design system for use measuring how a driver's biological information changes when the steering wheel is turned. The resulting information can then be used to help design a steering wheel that is more comfortable for the driver to use.

The present invention can be alternatively configured such that the heart beat analysis process is performed by the CPU 27 of the vehicle communications unit 26, the resulting electrocardiogram and other diagnostic information is successively displayed on a display monitor 32, heart beat data is stored to memory chronologically, and a warning device 31 is driven to warn the driver when a problem is detected. In this case, the results of the analysis processed in the vehicle communications unit 26 can be transmitted. Alternatively, it is not particularly necessary to provide the monitoring device 33.

Furthermore, while a heart beat detection means using the potential difference between a pair of electrodes 14 and 15 is shown in the preferred embodiment, it is alternatively possible to provide an infrared emitter and an infrared receptor on the steering wheel 2 so that both elements are touched when the driver holds the steering wheel 2, and blood pulse information is thus detected.

In addition, while the preferred embodiment of the invention has been described as detecting the heart beat as the biological information of interest, brain waves, blood pressure, and other biological signals can be detected.

It will also be obvious that the infrared receptor 8 and infrared emitters 9 and 10, and infrared emitter 11 and infrared receptors 12 and 13, can be respectively disposed to a side or bottom of the steering shaft 5 and steering column part 6, or to another desired location insofar as signals can be communicated between the respective elements.

It should also be noted that a magnetic sensor can be used as the position detection means, the heart beat data transmission device 7 can be built in to the steering wheel part 1, and the vehicle communications unit 26 can be located in the trunk or other place inside the vehicle.

As described above, it is possible by the present invention to reduce costs of retrofitting existing steering equipment, while preventing shorting or winding of a wire harness, when detecting vital biological status information received from sensors on the steering wheel.

It is also possible to maintain high quality wireless data transmission for transmitting vital biological status information detected from sensors on a motor vehicle steering wheel, utilizing a steering wheel position detector that allows data transmission when the steering wheel is in a certain position.

It will be apparent to those skilled in the art that various changes and modifications can be made in the biological information detection apparatus of the present invention without departing from the spirit or scope thereof. Thus, it is intended that the present invention cover the modifications and variations of this invention provided they come within the scope of the appended claims and their equivalents.

What is claimed is:

1. A biological information detection apparatus comprising:
    a biological information detection and transmission unit mounted on a steering wheel for detecting and transmitting biological information of an operator of a motor vehicle;
    a biological information receiver mounted on a steering column that receives biological information from the biological information detection and transmission unit; and
    a steering wheel position detector that detects a rotational position of the steering wheel; wherein
    the biological information detection and transmission unit comprises:
        a sensor for detecting biological information and generating a detection signal;
        memory for storing the detection signal from the sensor;
        a transmitter for transmitting a detection signal from the memory; and
        a controller for controlling the storage of the detection signal in memory and the transmitting of the detection signal from the transmitter when the steering wheel position detector detects that the steering wheel is in a substantially straight driving position; and
    the biological information receiver comprises a receiver which is mounted in a position whereby a detection signal from the transmitter can be received wirelessly when the steering wheel is in a substantially straight driving position.

2. The biological information detection apparatus as set forth in claim 1, wherein the receiver is mounted in a position opposite the transmitter when the steering wheel is in a substantially straight driving position.

3. The biological information detection apparatus as set forth in claim 1, wherein the transmitter contains a light-emitting element for transmitting the detection signal as an optical signal, and the receiver contains a receptor element for receiving said optical signal.

4. The biological information detection apparatus as set forth in claim 1, wherein the steering wheel position detector comprises at least one light-emitting element and receptor element pair disposed in opposition on the steering wheel and the steering column when the steering wheel is in a substantially straight driving rotational position.

5. The biological information detection apparatus as set forth in claim 1, further comprising a diagnostic unit which diagnoses a health-related condition of the operator based on the detection signal received by the receiver, and a notification unit which notifies the operator of the diagnostic result obtained by the diagnostic unit.

6. The biological information detection apparatus as set forth in claim 5, wherein the detection signal received by the receiver is wirelessly transmitted, and the diagnostic unit receives the wirelessly transmitted detection signal.

7. An apparatus for monitoring biological status information of a driver of a motor vehicle, comprising:
    at least one sensor adapted for detecting biological status information of a driver;
    a data transmission unit coupled to the at least one sensor, the data transmission unit comprising a clock generator, a CPU, a storage buffer, and a drive circuit;
    at least one pair of an emitter communication device and a receptor communication device, wherein each device is respectively positioned on one of a hub of a steering wheel and a steering column, such that the communication devices are aligned to be mutually opposed when the steering wheel is at a predetermined angle of rotation with respect to the steering column, and the communication device positioned on the hub of the steering wheel is coupled with the data transmission unit; and
    a vehicle communications unit coupled with the communication device positioned on the steering column, such that the vehicle communications unit is adapted to receive information generated by the data transmission unit; wherein
        biological status information detected by the at least one sensor is communicated between the data transmission unit and the vehicle communications unit through the at least one pair of the emitter communication device and the receptor communication device when the at least one pair are aligned to be mutually opposed, and the data transmission unit stores biological status information in the storage buffer when the at least one pair are not aligned to be mutually opposed.

8. The biological status monitoring apparatus of claim 7, wherein the vehicle communications unit further comprises an amplifier and transmitter for communicating information to an external monitoring device, and further comprises a receiver and a demodulator circuit for receiving and demodulating a warning signal generated from an external monitoring device.

9. The biological status monitoring apparatus of claim 8, wherein the vehicle communications unit further comprises a warning device and a display monitor for displaying a warning or the biological status information to the driver of the motor vehicle.

10. The biological status monitoring apparatus of claim 8, wherein the external monitoring device comprises a receiver and a demodulating circuit for demodulating a signal communicated from the vehicle communications unit, and further comprises a warning signal generator, coupled to an amplifier and a transmitter, for transmitting warning information to the vehicle communications unit.

11. The biological status monitoring apparatus of claim 7, wherein the at least one sensor is connected to the steering wheel of a motor vehicle.

12. The biological status monitoring apparatus of claim 11, further comprising a first electrode positioned at a first region on the steering wheel and a second electrode positioned at a second region on the steering wheel for detecting the biological status information by measuring the electrical potential difference between the electrodes.

13. The biological status monitoring apparatus of claim 12, wherein the first region is at one side of the steering wheel, and the second region is at the symmetrical opposite side of the steering wheel.

14. The biological status monitoring apparatus of claim 12, wherein the first and second regions are interspersed about the steering wheel.

15. The biological status monitoring apparatus of claim 7, wherein the biological status information comprises the heart beat rate of the driver of a motor vehicle.

16. The biological status monitoring apparatus of claim 7, wherein the biological status information comprises the brain wave signal of the driver of a motor vehicle.

17. The biological status monitoring apparatus of claim 7, wherein the biological status information comprises the blood pressure of the driver of a motor vehicle.

18. A biological status monitoring apparatus, comprising:
- a sensor for detecting biological status information of a driver of a motor vehicle;
- a data transmission unit coupled to the sensor;
- a plurality of emitter communication devices and receptor communication devices, positioned as pairs mutually opposed from each other on a steering wheel hub and a steering column when the steering wheel is at a predetermined alignment with respect to the steering column, such that each emitter communication device communicates with a respective receptor communication device, wherein the communication devices disposed on the steering wheel hub are coupled with the data transmission unit;
- a vehicle communications unit coupled with the communication devices disposed on the steering column; and
- an external monitoring device adapted for communication with the vehicle communications unit; wherein
    biological status information detected by the at least one sensor is communicated between the data transmission unit and the vehicle communications unit through the plurality of emitter communication devices and receptor communication devices when the steering wheel is at the predetermined alignment, and warning information determined from the biological status information is communicated between vehicle communications unit and the external monitoring device.

* * * * *